United States Patent
Ko

(10) Patent No.: US 10,626,110 B2
(45) Date of Patent: Apr. 21, 2020

(54) POLYMORPH OF PAZOPANIB HYDROCHLORIDE AND PREPARATION PROCESS THEREOF

(71) Applicant: FORMOSA LABORATORIES, INC., Taoyuan (TW)

(72) Inventor: Sheng-Kai Ko, Taoyuan (TW)

(73) Assignee: FORMOSA LABORATORIES, INC., Taoyuan (TW)

(*) Notice: Subject to any disclaimer, the term of this patent is extended or adjusted under 35 U.S.C. 154(b) by 0 days.

(21) Appl. No.: 16/056,619

(22) Filed: Aug. 7, 2018

(65) Prior Publication Data

US 2020/0048224 A1  Feb. 13, 2020

(51) Int. Cl.
 *C07D 403/12* (2006.01)
(52) U.S. Cl.
 CPC ........ *C07D 403/12* (2013.01); *C07B 2200/13* (2013.01)
(58) Field of Classification Search
 CPC .......................... C07D 239/42; C07D 401/12
 USPC ...................................................... 544/324
 See application file for complete search history.

(56) References Cited

U.S. PATENT DOCUMENTS

2016/0280689 A1* 9/2016 Chava .................. C07D 403/12

FOREIGN PATENT DOCUMENTS

| CN | 104130245 A | 11/2014 |
|---|---|---|
| CN | 103232443 B | 12/2014 |
| CN | 104557881 B | 8/2017 |
| CN | 107663193 A | 2/2018 |
| WO | 2011050159 A1 | 4/2011 |
| WO | 2011058179 A1 | 5/2011 |
| WO | 2011069053 A1 | 6/2011 |

OTHER PUBLICATIONS

Crystalline forms of 5-[[4-[(2, 3-Dimethyl-2H-indazol-6-yl) methylamino]-2-pyrimidinyl] amino]-2-methyl benzolsulfonamide and salts thereof, an IP.com Prior Art Database Technical Disclosure.

* cited by examiner

*Primary Examiner* — Venkataraman Balasubramanian
(74) *Attorney, Agent, or Firm* — Bacon & Thomas, PLLC

(57) ABSTRACT

The present disclosure provides a crystalline form F of Pazopanib HCl, which is characterized by an X-ray diffraction (XRD) pattern having peaks at about 11.3, 14.6, 16.9, 19.5, 19.7, 23.5 and 25.9°±0.2° 2θ. The present disclosure also provides a preparation process of a crystalline form F of Pazopanib HCl.

14 Claims, 3 Drawing Sheets

POLYMORPH OF PAZOPANIB HYDROCHLORIDE AND PREPARATION PROCESS THEREOF

BACKGROUND

1. Field

The present disclosure relates to a novel polymorph of Pazopanib hydrochloride (Pazopanib HCl) and preparation processes thereof.

2. Description of Related Art

Pazopanib is a tyrosine kinase inhibitor, which has been approved for treatments of renal cell carcinoma and soft tissue sarcoma. The structure of Pazopanib is represented by the following Formula (I):

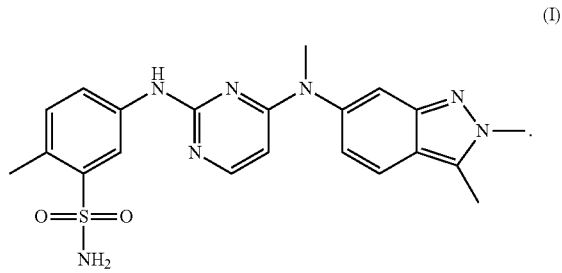

Patent publication No. WO 2011/069053A1 describes Form A of Pazopanib HCl and their preparation thereof. The XRD pattern of Pazopanib HCl Form A is shown in FIG. 1.

Even though different polymorphs have the same molecular formula, the physical properties thereof such as solubility may be greatly distinct. Thus, many researches have been developed to prepare novel polymorphic forms of Pazopanib HCl. It is known that Pazopanib HCl is usually formulated into oral tablets, thus the solubility of Pazopanib HCl in the acidic condition is one factor highly related to the dissolution of the pharmaceutical product containing Pazopanib HCl in the acidic condition.

Therefore, it is desirable to provide a novel polymorph of Pazopanib HCl with better physical properties to improve the performance characteristics of the pharmaceutical product containing Pazopanib HCl.

SUMMARY

The present disclosure relates to a novel polymorph of Pazopanib hydrochloride (Pazopanib HCl) and preparation processes thereof. Unexpectedly, the novel polymorph of Pazopanib HCl provided by the present disclosure has better solubility in an acidic condition compared to the crystalline form A of Pazopanib HCl.

An aspect of the present disclosure is drawn to a novel polymorph of Pazopanib HCl, named a crystalline form F of Pazopanib HCl, which is characterized by an X-ray diffraction (XRD) pattern having peaks at about 11.3, 14.6, 16.9, 19.5, 19.7, 23.5 and 25.9°±0.2° 2θ.

Another aspect of the present disclosure is a pharmaceutical composition, which comprises: the crystalline form F of Pazopanib HCl of the present disclosure; and a pharmaceutically acceptable carrier, excipient or diluent.

The pharmaceutical composition can be administered by oral administration. The pharmaceutical composition for oral administration can be any orally acceptable dosage form, including capsules, tablets, emulsions and aqueous suspensions, dispersions, and solutions. In the case of tablets, commonly used carriers include lactose and corn starch. Lubricating agents, such as magnesium stearate, are also typically added. For oral administration in a capsule form, useful diluents include lactose and dried corn starch. When aqueous suspensions or emulsions are administered orally, the active ingredient can be suspended or dissolved in an oily phase combined with emulsifying or suspending agents. If desired, certain sweetening, flavoring, or coloring agents can be added. Oral solid dosage forms can be prepared by spray dried techniques; hot melt extrusion strategy, micronization, and nano milling technologies.

The carrier, the excipient and the diluent in the pharmaceutical composition must be "acceptable" in the sense that it is compatible with the active ingredient of the composition (and preferably, capable of stabilizing the active ingredient) and not deleterious to the subject to be treated. One or more solubilizing agents can be utilized as pharmaceutical excipients for delivery of an active compound. Examples of other excipients include colloidal silicon dioxide, magnesium stearate, cellulose, sodium lauryl sulfate, and D&C Yellow #10.

Another aspect of the present disclosure is to provide a preparation process of a crystalline form F of Pazopanib HCl, comprising following steps: (a) mixing N-(2-chloro-pyrimidin-4-yl)-N,2,3-trimethyl-2H-indazol-6-amine (CPMI) and 5-amino-2-methylbenzenesulfonamide (AMBS) in a solvent to obtain a mixture, wherein the solvent comprises MeOH; (b) heating the mixture to react the CPMI with the AMBS; (c) distilling a portion of the solvent, and cooling the mixture to a temperature ranged from 0° C. to 20° C.; and (d) isolating solids from the mixture and drying the solids to give a crystalline form F of Pazopanib HCl.

A further another aspect of the present disclosure is to provide a preparation process of a crystalline form F of Pazopanib HCl, comprising following steps: (A) adding Pazopanib HCl with a crystalline form A into a solvent to obtain a mixture, wherein the solvent comprises MeOH; (B) stirring the mixture at room temperature for 48 hr or more; and (C) isolating solids from the mixture and drying the solids to give a crystalline form F of Pazopanib HCl.

Other novel features of the disclosure will become more apparent from the following detailed description when taken in conjunction with the accompanying drawings.

DETAILED DESCRIPTION

The present disclosure provides a novel polymorph of Pazopanib HCl.

One embodiment of the present disclosure is to provide a novel polymorph of Pazopanib HCl, named a crystalline form F, which is characterized by an X-ray diffraction (XRD) pattern having peaks at about 11.3, 14.6, 16.9, 19.5, 19.7, 23.5 and 25.9°±0.2° 2θ.

Another embodiment of the present disclosure is to provide the crystalline form F of Pazopanib HCl of the forgoing embodiment, wherein the XRD pattern further has peaks at about 17.3, 25.4 and 25.5°±0.2° 2θ.

Figure 2:
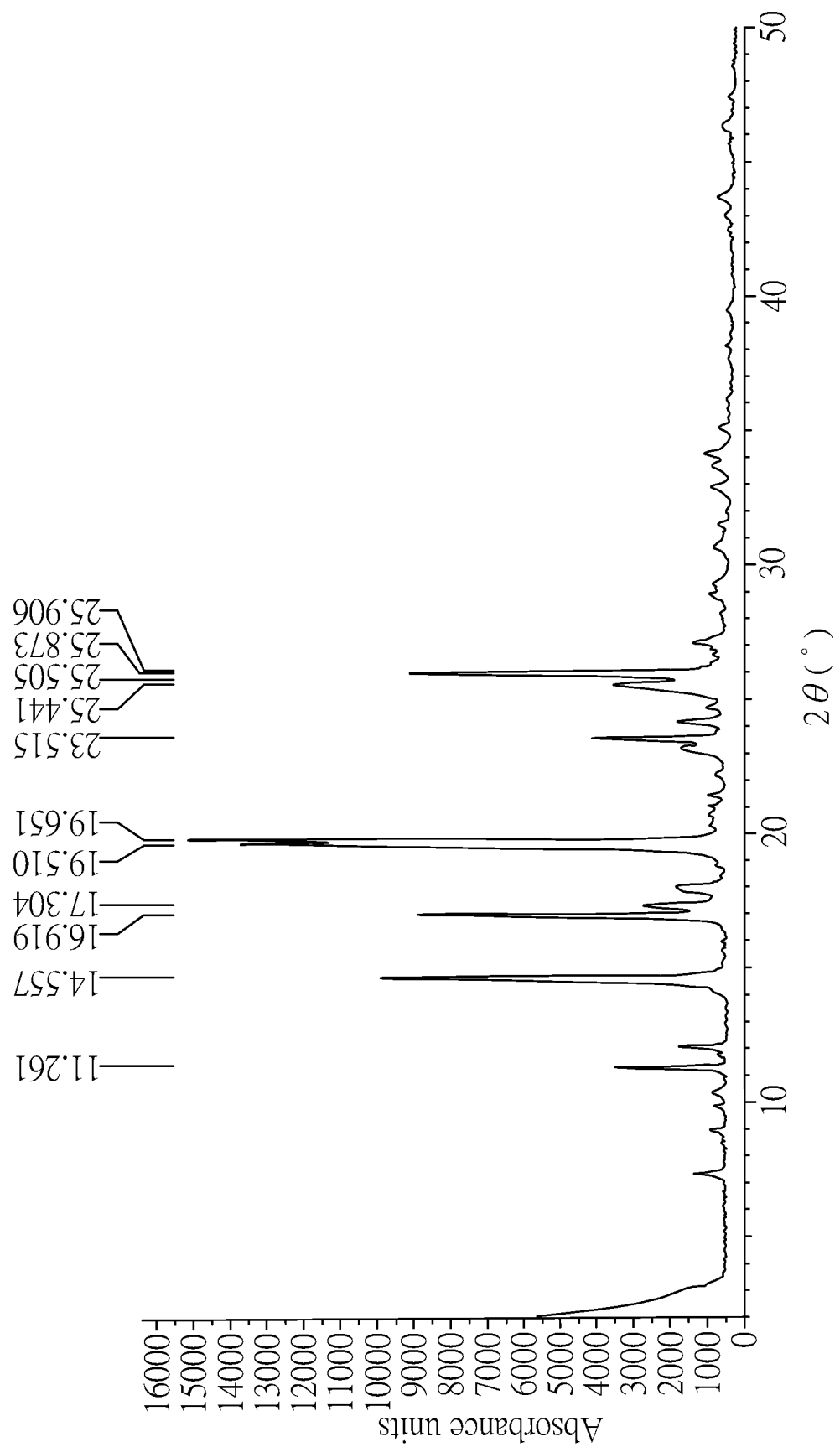
FIG. 2 is an X-ray diffraction (XRD) pattern of a crystalline form F of Pazopanib HCl.

Another embodiment of the present disclosure is to provide the crystalline form F of Pazopanib HCl of anyone of the forgoing embodiments, wherein the XRD pattern is substantially as depicted in FIG. 2.

Figure 3:
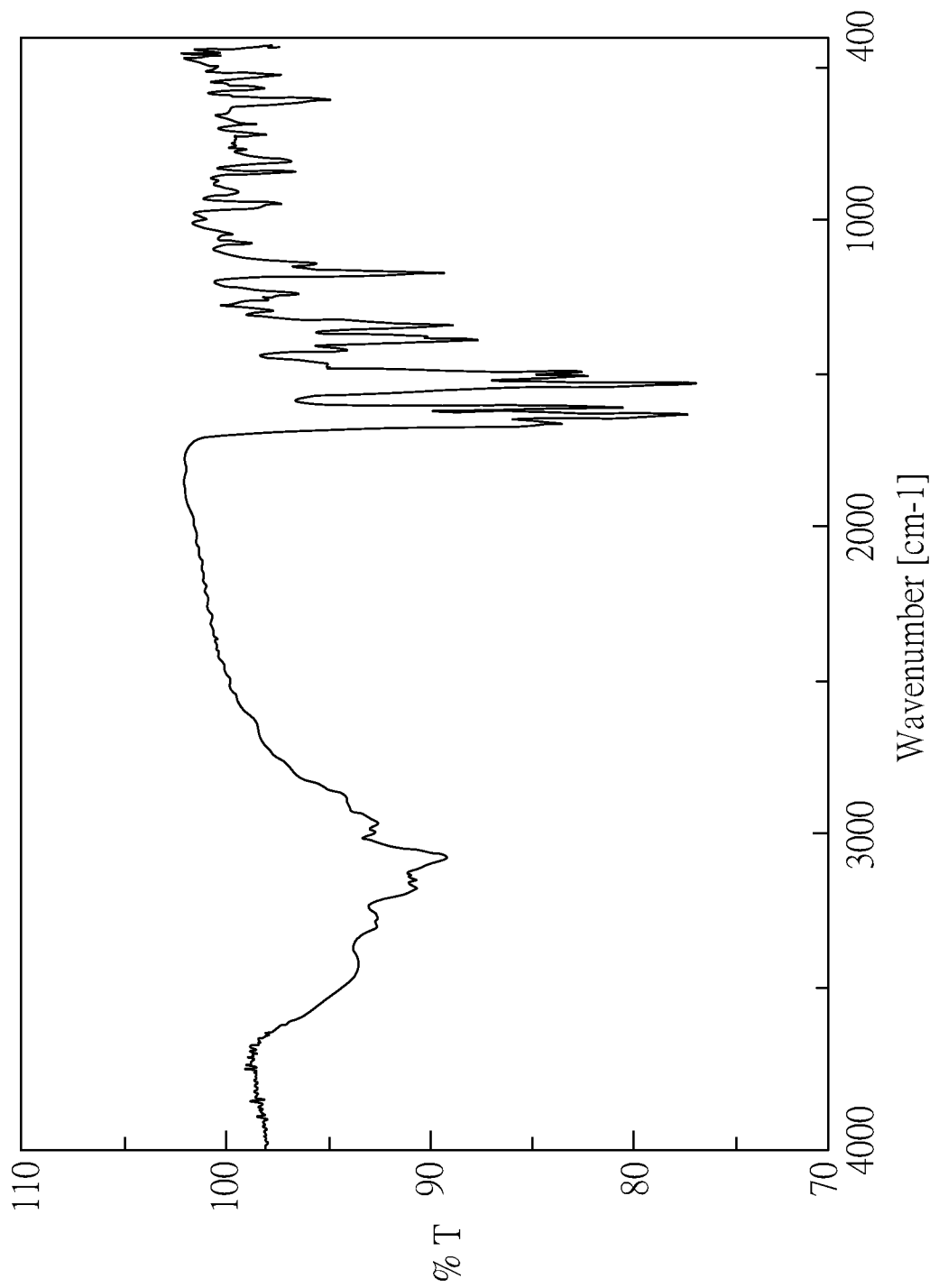
FIG. 3 is an infrared (IR) spectrum of a crystalline form F of Pazopanib HCl.

Another embodiment of the present disclosure is to provide the crystalline form F of Pazopanib HCl of anyone of the forgoing embodiments, wherein the crystalline form F of Pazopanib HCl is further characterized by an IR spectrum substantially depicted in FIG. 3.

The present disclosure also encompasses a preparation process of a novel polymorph of Pazopanib HCl, and especially the crystalline form F of Pazopanib HCl of anyone of the forgoing embodiments. This preparation process is performed by reacting N-(2-chloropyrimidin-4-yl)-N, 2,3-trimethyl-2H-indazol-6-amine (CPMI) with 5-amino-2-methyl benzenesulfonamide (AMBS) in a specific solvent system.

One embodiment of the present disclosure is to provide a preparation process of the crystalline form F of Pazopanib HCl of anyone of the forgoing embodiments, which may comprise the following steps: (a) mixing CPMI and AMBS in a solvent to obtain a mixture, wherein the solvent comprises MeOH; (b) heating the mixture to react the CPMI with the AMBS; (c) distilling a portion of the solvent, and cooling the mixture to a temperature ranged from 0° C. to 20° C.; and (d) isolating solids from the mixture and drying the solids to give a crystalline form F of Pazopanib HCl.

Another embodiment of the present disclosure is to provide the preparation process of the forgoing embodiment, wherein the mixture can be heated at reflux in the step (b).

Another embodiment of the present disclosure is to provide the preparation process of anyone of the forgoing embodiments, wherein the solvent used in the step (a) may selectively further comprise water. For example, in one embodiment of the present disclosure, the solvent may only comprise MeOH. In another embodiment of the present disclosure, the solvent may essentially comprises or be consisted of MeOH and water, and a volume ratio of MeOH to water may be ranged from 99.99:0.01 to 90:10.

Another embodiment of the present disclosure is to provide the preparation process of anyone of the forgoing embodiments, wherein the preparation process may further comprise a de-colorization step between the step (b) and the step (c). Herein, the color of the mixture may be removed by using any de-colorization agent, such as active carbon. In addition, the de-colorization step may be held under reflux. Furthermore, the solvent illustrated above may also be added into the mixture during the de-colorization step. Moreover, the de-colorization step may be performed for 2 hr or more. For example, the de-colorization step may be performed for 2 hr to 24 hr, 2 hr to 12 hr, 2 hr to 8 hr, 2 hr to 6 hr, 4 hr to 24 hr, 4 hr to 12 hr, 4 hr to 8 hr, or 4 hr to 6 hr.

Another embodiment of the present disclosure is to provide the preparation process of anyone of the forgoing embodiments, wherein the mixture may be cooled to a temperature from 0° C. to 20° C. For example, the mixture may be cooled to a temperature from 0° C. to 20° C., 0° C. to 15° C., 0° C. to 10° C., 5° C. to 20° C., 5° C. to 15° C. or 5° C. to 10° C.

Another embodiment of the present disclosure is to provide the preparation process of anyone of the forgoing embodiments, wherein the drying process in the step (d) may be held at 60° C. to 180° C. For example, the drying process may be held at 60° C. to 180° C., 70° C. to 160° C., 75° C. to 150° C., 85° C. to 140° C., 90° C. to 140° C., 95° C. to 140° C., 100° C. to 140° C., or 110° C. to 130° C. In addition, the time for performing the drying process is not particularly limited, as long as the solvent are approximately totally removed. For example, the drying process may be performed for 16 hr or more, 16 hr to 100 hr, 16 hr to 90 hr, 16 hr to 80 hr, 16 hr to 72 hr, 16 hr to 36 hr, or 16 hr to 24 hr.

The present disclosure also encompasses another preparation process of a novel polymorph of Pazopanib HCl, and especially the crystalline form F of Pazopanib HCl of anyone of the forgoing embodiments. This preparation process is performed by transferring the crystalline form A of Pazopanib HCl.

One embodiment of the present disclosure is to provide a preparation process of the crystalline form F of Pazopanib HCl of anyone of the forgoing embodiments, which may comprise the following steps: (A) adding Pazopanib HCl with a crystalline form A into a solvent to obtain a mixture, wherein the solvent comprises MeOH; (B) stirring the mixture at room temperature for 48 hr or more; and (C) isolating solids from the mixture and drying the solids to give a crystalline form F of Pazopanib HCl.

Another embodiment of the present disclosure is to provide the preparation process of anyone of the forgoing embodiments, wherein the solvent used in the step (A) may selectively further comprise water. For example, in one embodiment of the present disclosure, the solvent may only comprise MeOH. In another embodiment of the present disclosure, the solvent may essentially comprise or be consisted of MeOH and water, and a volume ratio of MeOH to water may be ranged from 99.99:0.01 to 90:10.

Another embodiment of the present disclosure is to provide the preparation process of the forgoing embodiment, wherein the mixture may be stirred at room temperature for 48 hr or more. For example, the mixture may be stirred at room temperature for 48 hr to 100 hr, 48 hr to 90 hr, 48 hr to 80 hr, 48 hr to 72 hr, 60 hr to 100 hr, 60 hr to 90 hr, 60 hr to 80 hr, or 60 hr to 72 hr.

Another embodiment of the present disclosure is to provide the preparation process of anyone of the forgoing embodiments, wherein the drying process in the step (C) may be held at 60° C. to 180° C. For example, the drying process may be held at 60° C. to 180° C., 60° C. to 160° C., 60° C. to 150° C., 60° C. to 140° C., 60° C. to 130° C., 60° C. to 120° C., 60° C. to 110° C., 65° C. to 100° C., 65° C. to 90° C., 65° C. to 85° C., 65° C. to 80° C., or 70° C. to 80° C. In addition, the time for performing the drying process is not particularly limited, as long as the solvent are approximately totally removed. For example, the drying process may be performed for 16 hr or more, 16 hr to 100 hr, 16 hr to 90 hr, 16 hr to 80 hr, 16 hr to 72 hr, 16 hr to 36 hr, or 16 hr to 24 hr.

The following examples when read with the accompanying drawings are made to clearly exhibit the above-mentioned and other technical contents, features and/or effects of the present disclosure. Through the exposition by means of the specific embodiments, people would further understand the technical means and effects the present disclosure adopts to achieve the above-indicated objectives. Moreover, as the contents disclosed herein should be readily understood and can be implemented by a person skilled in the art, all equivalent changes or modifications which do not depart from the concept of the present disclosure should be encompassed by the appended claims.

Furthermore, when a value is in a range from a first value to a second value, the value can be the first value, the second value, or another value between the first value and the second value.

EXAMPLE

Without further elaboration, it is believed that one skilled in the art can, based on the above description, utilize the present disclosure to its fullest extent. The following specific examples, i.e., EXAMPLES 1-3, are therefore to be construed as merely illustrative, and not limitative of the remainder of the disclosure in any way whatsoever.

Example 1

60 g CPMI was mixed with 42.72 g AMBS in 4200 ml MeOH, followed by heating to a reflux temperature. After the reaction was completed, 2400 ml MeOH was distilled and then the mixture was cooled to room temperature. The wet cake was de-colored with 4200 ml MeOH and 2.8 g active carbon at a reflux temperature for 4 hr. The mixture was hot filtered to remove the active carbon, and then 2700 ml MeOH was distilled. After distillation, the mixture was slowly cooled to 5~10° C. The solid was filtered and dried with Rotavapor at 120° C. to yield Pazopanib HCl Form F.

Example 2

Figure 1:
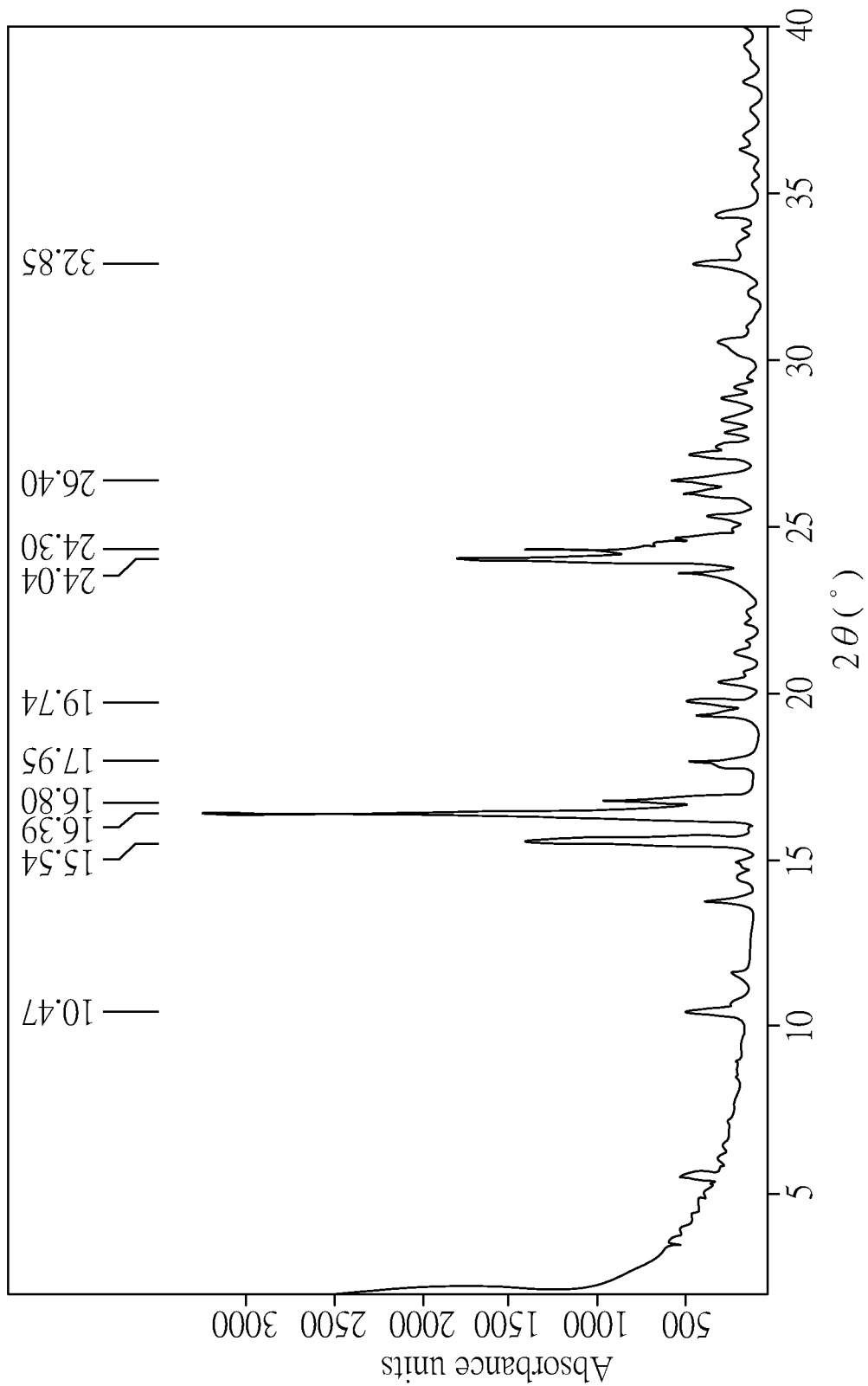
FIG. 1 is an X-ray diffraction (XRD) pattern of a crystalline form A of Pazopanib HCl.

10 g Pazopanib HCl Form A, which has an X-ray diffraction (XRD) pattern depicted in FIG. 1, was added into 150 ml MeOH and stirred at room temperature for 72 hr. Then, the solid was filtered out and dried at 70° C. for at least 16 hr to yield Pazopanib HCl Form F.

Example 3

10 g Pazopanib HCl Form A was added into MeOH/H$_2$O (in which a volume ratio of MeOH to H$_2$O was 95.3:4.7 and stirred at room temperature for 72 hr. Then, the solid was filtered out and dried at 70° C. for at least 16 hr to yield Pazopamib HCl Form F.

X-Ray Diffraction (XRD) Analysis 500 mg of samples obtained in EXAMPLES 1-3 was examined with X-ray diffraction spectrometer, Bruker D8 Advance. The parameters used in the XRD analysis are shown in the following Table 1.

TABLE 1

| XRD parameters | |
|---|---|
| Scan type | Normal |
| Voltage | 40 kV |
| Current | 35 mA |
| Scan range (2θ) | 2° to 50° |
| Step size | 0.02° |
| Time (sec) | 1 |

The XRD pattern of Pazopanib HCl Form F is shown in FIG. 2, which has peaks at about 11.3, 14.6, 16.9, 17.3, 19.5, 19.7, 23.5, 25.4, 25.5 and 25.9°±0.2° 2θ. The detail peak locations and intensities are listed in the following Table 2.

TABLE 2

| 2θ | Intensity |
|---|---|
| 11.261 | 20.0 |
| 14.557 | 64.4 |
| 16.919 | 57.3 |
| 17.304 | 15.1 |
| 19.510 | 90.1 |
| 19.651 | 100.0 |
| 23.515 | 23.7 |
| 25.441 | 17.9 |
| 25.505 | 19.8 |
| 25.873 | 50.6 |
| 25.906 | 57.8 |

As shown in FIG. 1 and FIG. 2, the XRD pattern of Pazopanib HCl Form F is totally different from the XRD pattern of Pazopanib HCl Form A. Thus, the present disclosure provides a novel polymorph of Pazopanib HCl.

Infrared (IR) Spectroscopy Analysis

Pazopanib HCl Form F was examined with IR spectroscopy analysis, JASCO FT/IR 460Plus. The analysis was preceded as described in United States Pharmacopeia (USP), spectrophotometric identification test <197K> and EP <2.2.24> Spectrophotometric Identification test. The IR spectrum of a potassium bromide (KBr) dispersion of the sample as shown in FIG. 3 exhibits the qualitatively similar to that of a Reference Spectrum.

Differential Scanning Calorimetry (DSC) Analysis

Mettler_Toledo DSC 2 STAR$^e$ system differential scanning calorimeter was used for the measurement. 10 mg of Pazopanib HCl Form F was heated from 100° C. to 325° C. at 10° C./min in a nitrogen atmosphere (60.0 ml/min), and the endothermic peak at around 291.75° C. can be found.

Solubility Analysis

The solubility of Pazopanib HCl Form F and Pazopanib HCl Form A in 0.1 M HCl and phosphate buffer (pH4.5 and pH6.8) was examined in the present analysis. The results are shown in the following Table 3.

TABLE 3

| | Pazopanib HCl Form A | Pazopanib HCl Form F |
|---|---|---|
| 0.1M HCl | Very slightly soluble (Solubility = 0.584 mg/ml) | Very slightly soluble (Solubility = 0.669 mg/ml) |
| Phosphate buffer, pH 4.5 | Practically insoluble | Practically insoluble |
| Phosphate buffer, pH 6.8 | Practically insoluble | Practically insoluble |

As shown in Table 3, Pazopanib HCl Form F has better solubility in 0.1 M HCl than Pazopanib HCl Form A. Because Pazopanib HCl is usually formulated into oral formulations, the dissolution of the oral pharmaceutical formulation can be increased in an acidic condition when Pazopanib HCl Form F with better solubility is used.

In conclusion, the present disclosure provides a novel polymorph of Pazopanib HCl, named Pazopanib HCl Form F, which can be prepared through a simple process. In addition, Pazopanib HCl Form F provided by the present disclosure has better solubility in an acidic condition compared to Pazopanib HCl Form A, and thus the application of Pazopanib HCl Form F in oral pharmaceutical formulations can further be improved. Furthermore, Pazopanib HCl Form F provided by the present disclosure also has better stability, and can be stored for a long time.

OTHER EXAMPLES

All of the features disclosed in this specification may be combined in any combination. Each feature disclosed in this specification may be replaced by an alternative feature serving the same, equivalent, or similar purpose. Thus, unless expressly stated otherwise, each feature disclosed is only an example of a generic series of equivalent or similar features.

Further, from the above description, one skilled in the art can easily ascertain the essential characteristics of the present disclosure, and without departing from the spirit and scope thereof, can make various changes and modifications of the disclosure to adapt it to various usages and conditions. Thus, other embodiments are also within the claims.

What is claimed is:

1. A crystalline form F of Pazopanib HCl, characterized by an X-ray diffraction (XRD) pattern having peaks at about 11.3, 14.6, 16.9, 19.5, 19.7, 23.5 and 25.9°±0.2° 2θ.

2. The crystalline form F of Pazopanib HCl of claim 1, wherein the XRD pattern further has peaks at about 17.3, 25.4 and 25.5°±0.2° 2θ.

3. The crystalline form F of Pazopanib HCl of claim 1, wherein the XRD pattern is substantially as depicted in FIG. 2.

4. The crystalline form F of Pazopanib HCl of claim 1, further characterized by an IR spectrum substantially depicted in FIG. 3.

5. A preparation process of a crystalline form F of Pazopanib HCl, comprising following steps:
 (a) mixing N-(2-chloropyrimidin-4-yl)-N,2,3-trimethyl-2H-indazol-6-amine (CPMI) and 5-amino-2-methyl-benzenesulfonamide (AMBS) in a solvent to obtain a mixture, wherein the solvent is a MeOH solvent or a MeOH-water solvent;
 (b) heating the mixture to react the CPMI with the AMBS at reflux;
 (b') adding MeOH into the mixture to de-coloring the mixture at reflux;
 (c) distilling a portion of MeOH, and cooling the mixture to a temperature ranged from 0° C. to 20° C.; and
 (d) isolating solids from the mixture and drying the solids to give a crystalline form F of Pazopanib HCl.

6. The preparation process of claim 5, wherein a volume ratio of MeOH to water in the MeOH-water solvent is ranged from 99.99:0.01 to 90:10.

7. The preparation process of claim 5, wherein the crystalline form F of Pazopanib HCl is characterized by an X-ray diffraction (XRD) pattern having peaks at about 11.3, 14.6, 16.9, 19.5, 19.7, 23.5 and 25.9°±0.2° 2θ.

8. The preparation process of claim 7, wherein the XRD pattern further has peaks at about 17.3, 25.4 and 25.5°±0.2° 2θ.

9. The preparation process of claim 7, wherein the XRD pattern is substantially as depicted in FIG. 2.

10. A preparation process of a crystalline form F of Pazopanib HCl, comprising following steps:
 (A) adding Pazopanib HCl with a crystalline form A into a solvent to obtain a mixture, wherein the solvent is a MeOH solvent or a MeOH-water solvent;
 (B) stirring the mixture at room temperature for 48 hr or more; and
 (C) isolating solids from the mixture and drying the solids to give a crystalline form F of Pazopanib HCl.

11. The preparation process of claim 10, wherein a volume ratio of MeOH to water in the MeOH-water solvent is ranged from 99.99:0.01 to 90:10.

12. The preparation process of claim 10, wherein the crystalline form F of Pazopanib HCl is characterized by an X-ray diffraction (XRD) pattern having peaks at about 11.3, 14.6, 16.9, 19.5, 19.7, 23.5 and 25.9°±0.2° 2θ.

13. The preparation process of claim 12, wherein the XRD pattern further has peaks at about 17.3, 25.4 and 25.5°±0.2° 2θ.

14. The preparation process of claim 12, wherein the XRD pattern is substantially as depicted in FIG. 2.

* * * * *